(12) United States Patent
Saalsaa

(10) Patent No.: US 8,494,868 B2
(45) Date of Patent: Jul. 23, 2013

(54) METHOD AND SYSTEM FOR A SEAMLESS INTERFACE BETWEEN AN EMERGENCY MEDICAL DISPATCH SYSTEM AND A NURSE TRIAGE SYSTEM

(75) Inventor: Richard Saalsaa, Salt Lake City, UT (US)

(73) Assignee: Priority Dispatch Corporation, Salt Lake City, UT (US)

( * ) Notice: Subject to any disclaimer, the term of this patent is extended or adjusted under 35 U.S.C. 154(b) by 558 days.

(21) Appl. No.: 10/140,635

(22) Filed: May 7, 2002

(65) Prior Publication Data

US 2003/0212575 A1    Nov. 13, 2003

(51) Int. Cl.
*G06Q 10/00*    (2006.01)

(52) U.S. Cl.
USPC .................................................. 705/2; 705/3

(58) Field of Classification Search
USPC .......................................... 705/1–3; 600/300
See application file for complete search history.

(56) References Cited

U.S. PATENT DOCUMENTS

| | | | |
|---|---|---|---|
| 3,799,147 A | 3/1974 | Adolph et al. | |
| 4,130,881 A | 12/1978 | Haessler et al. | |
| 4,164,320 A | 8/1979 | Irazoqui et al. | ............... 235/375 |
| 4,237,344 A | 12/1980 | Moore | |
| 4,290,114 A | 9/1981 | Sinay | |
| 4,338,493 A | 7/1982 | Stenhuis et al. | |
| 4,360,345 A | 11/1982 | Hon | |
| 4,455,548 A | 6/1984 | Burnett | |
| 4,489,387 A | 12/1984 | Lamb et al. | |
| 4,731,725 A | 3/1988 | Suto et al. | |
| 4,839,822 A | 6/1989 | Dormond et al. | |
| 4,858,121 A | 8/1989 | Barber et al. | |
| 4,865,549 A | 9/1989 | Sonsteby | ....................... 434/262 |
| 4,922,514 A | 5/1990 | Bergeron et al. | |
| 4,926,495 A | 5/1990 | Comroe et al. | |
| 4,945,476 A | 7/1990 | Bodick et al. | |
| 4,967,754 A | 11/1990 | Rossi | ............................. 128/670 |
| 5,063,522 A | 11/1991 | Winters | |
| 5,065,315 A | 11/1991 | Garcia | |
| 5,072,383 A | 12/1991 | Brimm et al. | ............. 364/413.02 |
| 5,077,666 A | 12/1991 | Brimm et al. | ............. 364/413.02 |
| 5,086,391 A | 2/1992 | Chambers | |
| 5,109,399 A | 4/1992 | Thompson | |
| 5,122,959 A | 6/1992 | Nathanson et al. | |
| 5,193,855 A | 3/1993 | Shamos | ........................ 283/117 |
| 5,228,449 A | 7/1993 | Christ et al. | |
| 5,253,164 A | 10/1993 | Holloway et al. | |
| 5,255,187 A | 10/1993 | Sorensen | |
| 5,291,399 A | 3/1994 | Chaco | ....................... 364/413.02 |
| 5,323,444 A | 6/1994 | Ertz et al. | |

(Continued)

OTHER PUBLICATIONS

Anonymous, Suburban Chicago towns centralize 911 services, Oct. 1994, Communications News, vol. 31 No. 10, pp. 443.*

(Continued)

*Primary Examiner* — Robert Morgan
*Assistant Examiner* — Michael Fuelling
(74) *Attorney, Agent, or Firm* — Stoel Rives, LLP

(57) ABSTRACT

A method and system for integrating an emergency medical dispatch system with a nurse triage system that includes a health reference library and which seamlessly maintains information for use by both the emergency medical dispatch system and the nurse triage system. This invention enhances the quality of provided medical services by providing a consistent, reliable technique for collecting, evaluating and dispensing medical information and for evaluating a medical condition for subsequent medical dispatch and/or care.

29 Claims, 3 Drawing Sheets

U.S. PATENT DOCUMENTS

| | | | |
|---|---|---|---|
| 5,339,351 A | 8/1994 | Hoskinson et al. | |
| 5,348,008 A | 9/1994 | Bornn et al. | |
| 5,379,337 A | 1/1995 | Castillo et al. | |
| 5,404,292 A | 4/1995 | Hendrickson | |
| 5,410,471 A | 4/1995 | Alyfuku et al. | 364/413.02 |
| 5,423,061 A | 6/1995 | Fumarolo et al. | |
| 5,438,996 A | 8/1995 | Kemper et al. | |
| 5,441,047 A | 8/1995 | David et al. | 128/670 |
| 5,462,051 A | 10/1995 | Oka et al. | |
| 5,471,382 A | 11/1995 | Tallman et al. | 364/406 |
| 5,502,726 A | 3/1996 | Fischer | |
| 5,513,993 A | 5/1996 | Lindley et al. | |
| 5,516,702 A | 5/1996 | Senyei et al. | |
| 5,521,812 A | 5/1996 | Feder et al. | |
| 5,536,084 A | 7/1996 | Curtis et al. | 364/413.01 |
| 5,544,649 A | 8/1996 | David et al. | 128/630 |
| 5,554,031 A | 9/1996 | Moir et al. | |
| 5,590,269 A | 12/1996 | Kruse et al. | |
| 5,594,638 A | 1/1997 | Iliff | |
| 5,594,786 A | 1/1997 | Chaco et al. | 379/93 |
| 5,596,994 A | 1/1997 | Bro | |
| 5,630,125 A | 5/1997 | Zellweger | |
| 5,636,873 A | 6/1997 | Sonsteby | 283/81 |
| 5,650,995 A | 7/1997 | Kent | |
| 5,660,176 A | 8/1997 | Iliff | |
| 5,675,372 A | 10/1997 | Aguayo, Jr. et al. | |
| 5,682,419 A | 10/1997 | Grube et al. | |
| 5,684,860 A | 11/1997 | Milani et al. | |
| 5,689,229 A | 11/1997 | Chaco et al. | 340/286.07 |
| 5,719,918 A | 2/1998 | Serbetciouglu et al. | |
| 5,722,418 A | 3/1998 | Bro | |
| 5,724,983 A | 3/1998 | Selker et al. | |
| 5,734,706 A | 3/1998 | Windsor et al. | |
| 5,745,532 A | 4/1998 | Campana, Jr. | |
| 5,748,907 A | 5/1998 | Crane | 395/202 |
| 5,754,960 A | 5/1998 | Downs et al. | |
| 5,759,044 A | 6/1998 | Redmond | |
| 5,761,278 A | 6/1998 | Pickett et al. | |
| 5,761,493 A | 6/1998 | Blakeley et al. | |
| 5,787,429 A | 7/1998 | Nikolin, Jr. | |
| 5,805,670 A | 9/1998 | Pons et al. | |
| 5,809,493 A | 9/1998 | Ahamed et al. | |
| 5,822,544 A | 10/1998 | Chaco et al. | 395/202 |
| 5,823,948 A | 10/1998 | Ross, Jr. et al. | 600/300 |
| 5,826,077 A | 10/1998 | Blakeley et al. | |
| 5,832,187 A | 11/1998 | Pedersen et al. | |
| 5,842,173 A | 11/1998 | Strum et al. | 705/1 |
| 5,844,817 A | 12/1998 | Lobley et al. | |
| 5,850,611 A * | 12/1998 | Krebs | 455/518 |
| 5,857,966 A | 1/1999 | Clawson | 600/300 |
| 5,901,214 A | 5/1999 | Shaffer et al. | |
| 5,902,234 A | 5/1999 | Webb | |
| 5,910,987 A | 6/1999 | Ginter et al. | |
| 5,912,818 A | 6/1999 | McGrady et al. | 364/479.02 |
| 5,915,019 A | 6/1999 | Ginter et al. | |
| 5,926,526 A | 7/1999 | Rapaport et al. | |
| 5,933,780 A | 8/1999 | Connor et al. | |
| 5,961,446 A | 10/1999 | Beller et al. | 600/300 |
| 5,962,891 A | 10/1999 | Arai | |
| 5,964,700 A * | 10/1999 | Tallman et al. | 600/300 |
| 5,986,543 A | 11/1999 | Johnson | |
| 5,989,187 A | 11/1999 | Clawson | 600/300 |
| 5,991,730 A | 11/1999 | Lubin et al. | 705/3 |
| 5,991,751 A | 11/1999 | Rivette et al. | |
| 6,004,266 A | 12/1999 | Clawson | 600/300 |
| 6,010,451 A | 1/2000 | Clawson | 600/300 |
| 6,022,315 A | 2/2000 | Iliff | |
| 6,035,187 A * | 3/2000 | Franza | 455/404.1 |
| 6,040,770 A | 3/2000 | Britton | |
| 6,052,574 A | 4/2000 | Smith, Jr. | |
| 6,053,864 A | 4/2000 | Clawson | 600/300 |
| 6,058,179 A | 5/2000 | Shaffer et al. | |
| 6,074,345 A | 6/2000 | van Oostrom et al. | |
| 6,076,065 A | 6/2000 | Clawson | 705/2 |
| 6,078,894 A | 6/2000 | Clawson et al. | 705/11 |
| 6,106,459 A * | 8/2000 | Clawson | 600/300 |
| 6,112,083 A | 8/2000 | Sweet et al. | |
| 6,115,646 A | 9/2000 | Fiszman et al. | |
| 6,117,073 A * | 9/2000 | Jones et al. | 600/300 |
| 6,118,866 A | 9/2000 | Shtivelman | |
| 6,127,975 A | 10/2000 | Maloney | |
| 6,134,105 A | 10/2000 | Lueker | |
| 6,292,542 B1 * | 9/2001 | Bilder | 379/45 |
| 6,370,234 B1 | 4/2002 | Kroll | |
| 6,535,121 B2 | 3/2003 | Matheny | |
| 6,607,481 B1 | 8/2003 | Clawson | |
| 6,879,819 B2 | 4/2005 | Brooks | |
| 6,901,397 B1 | 5/2005 | Moldenhauer et al. | |
| 6,931,112 B1 | 8/2005 | McFarland et al. | |
| 6,968,375 B1 | 11/2005 | Brown | |
| 7,106,835 B2 | 9/2006 | Saalsaa | |
| 2002/0004729 A1 * | 1/2002 | Zak et al. | 705/3 |
| 2002/0106059 A1 | 8/2002 | Kroll et al. | |
| 2003/0028536 A1 | 2/2003 | Singh et al. | |
| 2003/0212575 A1 | 11/2003 | Saalsaa et al. | |
| 2006/0178908 A1 * | 8/2006 | Rappaport | 705/2 |
| 2007/0055559 A1 | 3/2007 | Clawson | |
| 2007/0116189 A1 | 5/2007 | Clawson | |

OTHER PUBLICATIONS

Radosevich, Lynda, "Network holds sway on life, death," Computerworld, v27 n21, May 24, 1993, 2 pgs.

Harris, Roger, "Updated 911 Phone System Top Concern of Residents," Business First-Louisville, v9 n19 s1, Dec. 1992, 3 pgs.

"Geac Completes Software Install," Wireless Week, Nov. 18, 1996, 3 pgs.

"Dictaphone introduces Windows-based Computer-Aided Dispatch (CAD) system," Business Wire, Apr. 23, 1996, 2 pgs. (in commercial use in 1995).

Holroyd, Brian, et al., "Medical Control; Quality Assurance in Prehospital Care," JAMA, the Journal of American Medical Association, v256, n8, Aug. 1986, p. 1027-1031.

CBS web page News Story entitled "911 Operator: 'It's got to be Hell'", Mar. 31, 2006 (excerpts from 911 operators' actions during the attacks on Sep. 11, 2001), 3 pgs.

Best, Wendy, "999 United Emergency services share life-saving Role to boost response," Western Daily Press, WDP Severnside ed., May 27, 1999, 2 pgs.

Poellmitz, William C., "Wireless technology keeps public safety a step ahead," Nation's Cities Weekly, v21 n17, Apr. 27, 1998, 3 pgs.

Crowley, Mark, "Learning from CAD System Implementation," Communications, v29 n8, Aug. 1992, 5 pgs.

Office Action Summary from USPTO for U.S. Appl. No. 10/255,901 mailed Dec. 31, 2003, 8 pgs.

Office Action Summary from USPTO for U.S. Appl. No. 10/255,901 mailed Oct. 13, 2004, 8 pgs.

Office Action Summary from USPTO for U.S. Appl. No. 10/255,901 mailed Jun. 29, 2005, 7 pgs.

Advisory Action Before the Filing of an Appeal Brief from USPTO for U.S. Appl. No. 10/255,901 mailed Feb. 14, 2006, 3 pgs.

Office Action Summary from USPTO for U.S. Appl. No. 10/255,901 mailed Jun. 7, 2006, 8 pgs.

Office Action Summary from USPTO for U.S. Appl. No. 10/255,901 mailed Feb. 27, 2007, 8 pgs.

Office Action Summary from USPTO for U.S. Appl. No. 10/255,901 mailed Sep. 6, 2007, 9 pgs.

Office Action Summary from USPTO for U.S. Appl. No. 10/255,905 mailed May 19, 2004, 7 pgs.

Office Action Summary from USPTO for U.S. Appl. No. 10/255,905 mailed May 26, 2005, 5 pgs.

Office Action Summary from USPTO for U.S. Appl. No. 10/255,905 mailed Feb. 9, 2006, 8 pgs.

Advisory Action Before the Filing of an Appeal Brief from USPTO for U.S. Appl. No. 10/255,905 mailed Aug. 11, 2006, 3 pgs.

Office Action Summary from USPTO for U.S. Appl. No. 10/255,905 mailed Jan. 30, 2007, 7 pgs.

Office Action Summary from USPTO for U.S. Appl. No. 10/255,905 mailed Oct. 5, 2007, 7 pgs.

Office Action Summary from USPTO for U.S. Appl. No. 09/685,697 mailed Jul. 18, 2003, 8 pgs.

Office Action Summary from USPTO for U.S. Appl. No. 09/685,697 mailed Feb. 3, 2004, 5 pgs.
Office Action Summary from USPTO for U.S. Appl. No. 09/685,697 mailed Jan. 4, 2005, 5 pgs.
Office Action Summary from USPTO for U.S. Appl. No. 09/685,697 mailed Oct. 4, 2005, 7 pgs.
Advisory Action Before the Filing of an Appeal Brief from USPTO for U.S. Appl. No. 09/685,697 mailed Mar. 13, 2006, 4 pgs.
Office Action Summary from USPTO for U.S. Appl. No. 09/685,697 mailed Jun. 26, 2006, 8 pgs.
Office Action Summary from USPTO for U.S. Appl. No. 09/685,697 mailed Apr. 10, 2007, 9 pgs.
Office Action Summary from USPTO for U.S. Appl. No. 09/685,697 mailed Oct. 9, 2007, 11 pgs.

* cited by examiner

METHOD AND SYSTEM FOR A SEAMLESS INTERFACE BETWEEN AN EMERGENCY MEDICAL DISPATCH SYSTEM AND A NURSE TRIAGE SYSTEM

BACKGROUND OF INVENTION

1. Field of the Invention

This invention relates to methods and systems for collecting medical related information from callers. More specifically, this invention relates to methods and systems for collected health information by prompting medical professionals to collect specific information, that systematically determines the level of health services and/or emergency medical response that is required and that provides consistent specific information based medical gate-keeper or triage function.

2. Description of Related Art

A variety of methods and systems have been described that address automated medical information systems, emergency medical dispatch management, or can be used to assess the skills of the medical personnel. However, generally, these prior systems do not provide an integrated intimate clinical link between the nurse triage functions and the emergency medical dispatch system and therefore, do not provide a consistent integration of information collection, and often require call receivers (dispatchers or nurses) to pass the caller to other call responders who then must begin anew to collect information that is at best redundant and which is often contradictory. The use of prior systems alone may lead to confusion and the corresponding disbursal of inaccurate information to callers.

U.S. Pat. No. 4,164,320 describes an element suitable for attachment to a hospital wristband or patient specimen container, which element has a coating of magnetizable material that is encoded along a circular track with patient identification and other desired information relating to the patient and the system employing such elements.

U.S. Pat. No. 4,865,549 describes a documentation system that allows adequate control of documentation in addition to an assessment of skills of the professionals involved, which includes a plurality of sections, each section dedicated to a particular body system.

U.S. Pat. No. 4,967,754 describes an apparatus and method for anticipating the side effects, which are manifested in a patient during a dialysis treatment.

U.S. Pat. Nos. 5,072,383 and 5,077,666 describe hospital information systems that comprises a data processing system including a plurality of terminals having display means and data entry means.

U.S. Pat. No. 5,193,855 describes a patient and healthcare provider identification system that includes a database of patient and healthcare provider information.

U.S. Pat. No. 5,291,399 describes a distributed data processing network that includes multiple memory card databases at terminal nodes of the network.

U.S. Pat. No. 5,410,471 describes a networked health care and monitoring system capable of providing an updated reliable vital information on the health condition of individuals and adapted to support home health care and maintenance.

U.S. Pat. No. 5,471,382 describes a medical network management system, which health plan beneficiaries access a team of health care professionals over the telephone to help them assess their health needs and select appropriate care.

U.S. Pat. No. 5,536,084 describes a mobile nursing unit that comprises a cart which stores and transports medications and medical supplies and a computer system mounted on the cart for transmitting and receiving data as a nurse performs patient rounds.

U.S. Pat. Nos. 5,441,047 and 5,544,649 describe an ambulatory patient health monitoring systems where the patient is monitored by a health care worker at a central station, while the patient is at a remote location.

U.S. Pat. No. 5,636,873 describes a documentation system that allows adequate control of documentation in addition to an assessment of skills of the professionals involved that includes a plurality of pads, each notepad dedicated to a particular disease process or body system.

U.S. Pat. Nos. 5,594,786 and 5,689,229 describe patient care and communication systems which uses a central processing system and a plurality of remote stations electrically connected to the central processing system to facilitate visual and data communications.

U.S. Pat. No. 5,748,907 describes an interactive dynamic real-time management system that includes a microprocessor adapted to sense the automatic interaction of real-time inputs relating to the method of controlling the position, flow of patients, employees, invoicing, appointment scheduling, and financial costs; also controlling of time, space, and tasks automatically of a medical clinic or other types of businesses.

U.S. Pat. No. 5,822,544 describes a patient care and communication system, which utilizes a central processing system, and a plurality of remote stations electronically connected to the central processing system to facilitate audio, visual and data communications.

U.S. Pat. No. 5,823,948 describes a system that provides automatic incorporation of dictated text/medical records summary generation in medical English text; parsing dictation to data; parsing dictation to data; prephrased text, automatic generation of medical record as a consequence of data entry and similar features of a medical records, documentation, tracking and order entry system.

U.S. Pat. No. 5,842,173 describes a computer-based surgical services management system for communicating between sites of a surgical services facility including a computer workstation located at each site of the facility, a server in network communication with each workstation, and a database resident on the network.

U.S. Pat. No. 5,912,818 describes a system for monitoring and dispensing medical items, which are dispensed for administration to patients that includes a data terminal connected through a network to at least one remote computer.

U.S. Pat. No. 5,961,446 describes a teleconferencing system that uses video conferencing between a nurse station and a patient station to deliver medical care.

U.S. Pat. No. 5,991,730 describes a method and system for patient flow tracking through a medical clinic and wherein data is acquired from the automated patient flow tracking.

U.S. Pat. No. 5,857,966 describes a method and system for receiving processing and responding to emergency medical calls for patients who have fainted or are unconscious.

U.S. Pat. No. 5,989,187 describes a method and system for providing emergency medical counseling to childbirth patients remotely.

U.S. Pat. No. 6,004,266 describes a method and system for receiving, processing and responding to emergency medical calls for patients with heart problems.

U.S. Pat. No. 6,010,451 describes a method and system for providing emergency medical counseling to choking patients remotely.

U.S. Pat. No. 6,053,864 describes a method and system for providing emergency medical counseling to arrest patients remotely.

U.S. Pat. No. 6,076,065 describes a method and system for receiving, processing and responding to emergency medical calls for patients with pregnancy related medical problems.

U.S. Pat. No. 6,078,894 describes a method and system for evaluating the performance of emergency medical dispatchers in adhering to a provided systematic procedure or protocol for handling emergency medical calls.

U.S. Pat. No. 6,106,459 describes a method and system for receiving, processing and responding to emergency medical calls by emergency medical dispatchers.

SUMMARY OF INVENTION

It is desirable to provide a method and system for interfacing an emergency medical dispatch system with a nurse triage system. It is particularly useful to provide an interface method and system that maintains collected information from one of the systems for use in the other system, that provides a consistent user interface, and that provides the capability of multiple transition points between the emergency medical dispatch system and the nurse triage system.

Accordingly, it is an object of this invention to provide a method and system for interfacing an emergency medical dispatch system with a nurse triage system.

Another object of this invention is to provide a method and system for interfacing an emergency medical dispatch system with a nurse triage system that maintains information gathered by the emergency medical dispatch system for use in the nurse triage system.

Another object of this invention is to provide a method and system for interfacing an emergency medical dispatch system with a nurse triage system that maintains information gathered by the nurse triage system for use in the emergency medical dispatch system.

A further object of this invention is to provide a method and system for interfacing an emergency medical dispatch system with a nurse triage system that provides a consistent user interface.

A still further object of this invention is to provide a method and system for interfacing an emergency medical dispatch system with a nurse triage system that permits multiple transition points between the two systems.

It is another object of this invention to provide a method and system for interfacing an emergency medical dispatch system with a nurse triage system that prompts medical professionals to collect specific information.

It is a further object of this invention to provide a method and system for interfacing an emergency medical dispatch system with a nurse triage system that uses the collected information to determine the appropriate level of health services that are required.

It is a still further object of this invention to provide a method and system for interfacing an emergency medical dispatch system with a nurse triage system that streamlines communication between emergency public safety systems, phone-based health care gatekeeper systems and health care providers.

Another object of this invention is to provide a method and system for interfacing an emergency medical dispatch system with a nurse triage system that in some embodiments can be configured in a stand-alone mode for use in emergency call centers or in traditional nurse triage centers.

Additional objects, advantages and other novel features of this invention will be set forth in part in the description that follows and in part will become apparent to those skilled in the art upon examination of the following or may be learned with the practice of the invention. The objects and advantages of this invention may be realized and attained by means of the instrumentalities, combinations and steps particularly pointed out in the appended claims. Still other objects of the present invention will become readily apparent to those skilled in the art from the following description wherein there is shown and described present preferred embodiments of this invention, simply by way of illustration of the best modes presently known to the inventors for carrying out this invention. As will be realized, this invention is capable of other different embodiments, and its several details and steps are capable of modification in various aspects without departing from the invention. Accordingly, the objects, drawings and descriptions should be regarded as illustrative in nature and not as restrictive.

To achieve the foregoing and other objectives, a computerized interface process and system is provided.

BRIEF DESCRIPTION OF DRAWINGS

The accompanying drawings incorporated in and forming a part of the specification, illustrate a preferred embodiment of the present invention. Some, although not all, alternative embodiments are described in the following description.

In the drawings.

Figure 1:
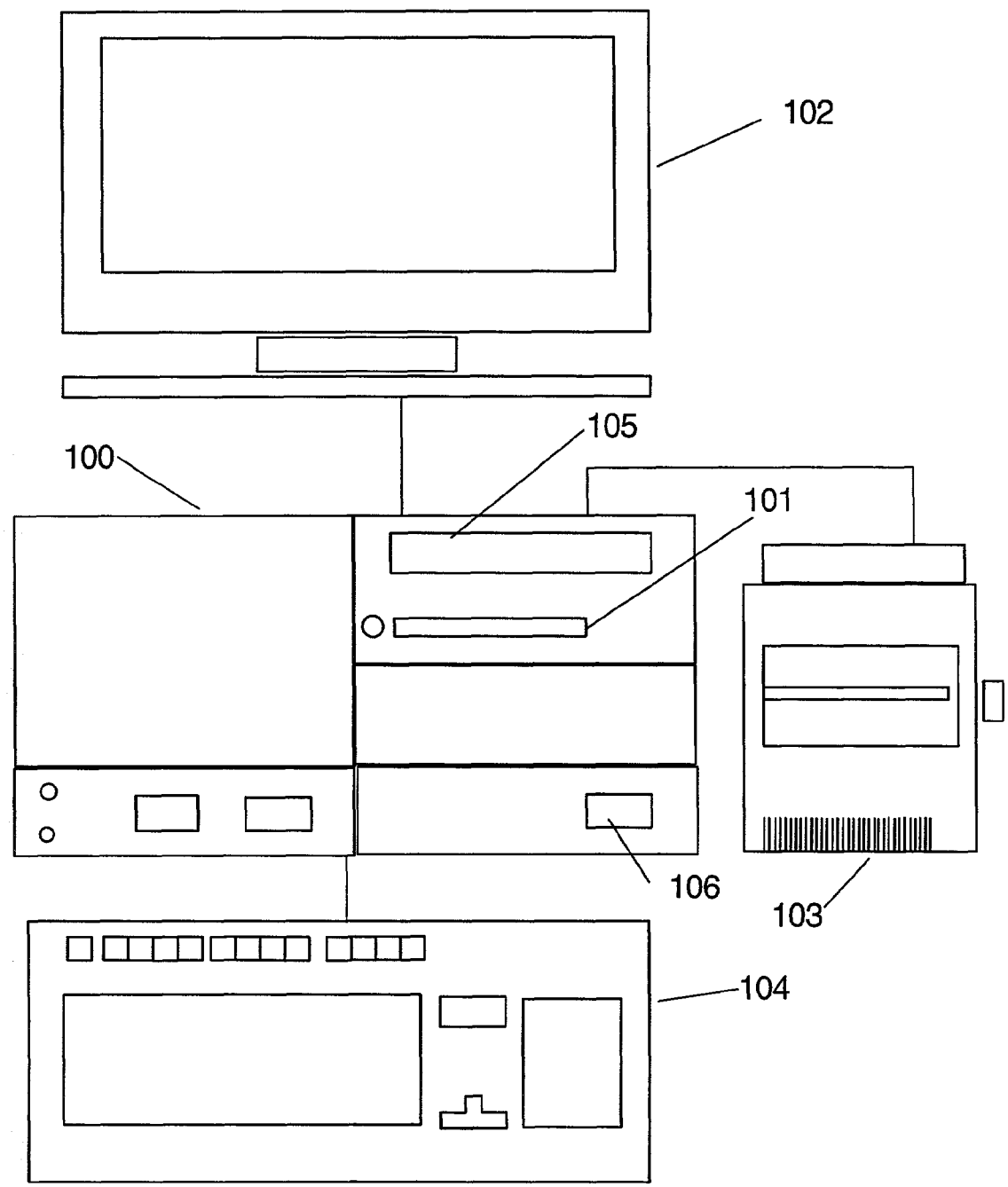
FIG. 1 is a top-level computer system diagram showing the major computer system components used in the present embodiment of the invention.

Reference will now be made in detail to the present preferred embodiment of the invention, an example of which is illustrated in the accompanying drawings.

DETAILED DESCRIPTION

This concerns a method and system for interfacing an emergency medical dispatch system with a nurse triage system, that provides consistency and reliability of information provided to callers and dispatched emergency medical personnel by using a computerized system in combination with a voice communication system and databases containing health reference information and patient medical information.

In most prior health systems, the processes by which individuals access medical care services are notably inefficient. Such inefficiency causes delays and errors in the provision of potentially life-saving treatments in some cases, and results in the use of unnecessarily expensive or risky interventions in others. It is not surprising that access to health care poses a daunting challenge to traditional health service systems. For one thing, people do not become ill or develop a need for health information on a scheduled basis. This means that health systems must cope with inherently unpredictable demands for services. In addition, the correct matching of an individual's health care needs with an appropriate level of service requires that information be obtained from the persons before he/she enters the system, and that a sufficiently broad spectrum of service options be available once the appropriate level of care has been determined. Unfortunately, prior to this invention, there are few standardized, proven safe-and-effective methods by which to ascertain the appropriate level of service for a particular individual, and even where this problem has been addressed, the typical prior methods are not generally linked with a provider system that affords a sufficiently robust spectrum of services. In recent times, most health systems have experienced an unprecedented increase in demand for services. In developed countries, this increase has been caused by an aging populations, increased health-seeking behavior and increasing numbers of immigrants. In less developed countries, the increase is often driven by epidemics of communicable diseases as well as increased availability of life saving medications. Even as the demand for health care services has increased, the supply of such services has tended to diminish. This contraction is due to both cost-driven reductions in the number of acute care hospitals and ambulance providers, and to an accelerating shortage of qualified nurses. Often those provides who remain are required by law to provide services to those who dial nationally recognized emergency access numbers or who otherwise arrive in an Emergency Department (ED) and the resulting increased burden to the medical service providers is not always mitigated by appropriate reimbursement for such services. As a result of the widening gap between the demand for and the supply of health services, many EDs and ambulance transportation services are now operating at or beyond critical capacity.

This invention addresses this problem by providing an integrated solution for collecting specific health information from callers by prompting trained medical professional appropriately, for using this collected information to determine the appropriate level of health services that are required, for managing nurse triage processes and for providing requested health information. Although designed to operate in a full-integrated manner, this invention can be configured for stand-alone use in emergency call centers or in traditional nurse triage centers.

At the core of this invention is an interface between call communications devices, an emergency medical dispatch protocol and criticality determination system, a nurse triage system and a health reference library, that maintains patient information as the process transitions between each of these systems and that provides a computerized process for ensuring consistency, reliability, accuracy, control and management.

FIG. 1 shows a top level computer system diagram showing the major computer system 100 components used in the present embodiment of the invention. In is present preferred embodiment, the method of this invention operates on a computer system 100, typically having the following components in communication with the computer processor 101, which is presently a Pentium III, 1 GHz processor running the Windows 2000 or XP Professional operating system, although alternative processors and operating systems can be substituted without departing from the concept of this invention. A viewable display 102, presently typically a 17" TFT compliant XGA monitor having 1024×768 resolution, is in communication with the processor 101. The present computer system 100 used in this invention is configured with 256 Mbytes of RAM and 10 Gbytes of hard disk space 105. A 100 Mbit Ethernet LAN adapter 106, in communication with the processor 101 is also provided in the present invention for a network communication connection. A keyboard/mouse 104 input device, also in communication with the processor 105 is provided for user control and input. And a hardcopy printer 103, in communication with the computer 100 processor 105 is provided for production of reports and other paper information. The present embodiment of the invention uses Microsoft SQL (version 7.0 or 2000); Crystal Reports version 8.5 for the reports engine. The present embodiment of the interface component of the invention is written in Microsoft Visual Basic. The dispatch determination software is written in Delphi. The present software embodiment of this invention is compatible with a workstation environment, using a centralized server that can be replicated for rapid recovery should there be a catastrophic failure of the equipment. The databases used in the system of this invention are presently available in ASCII and XML formats.

Figure 2:
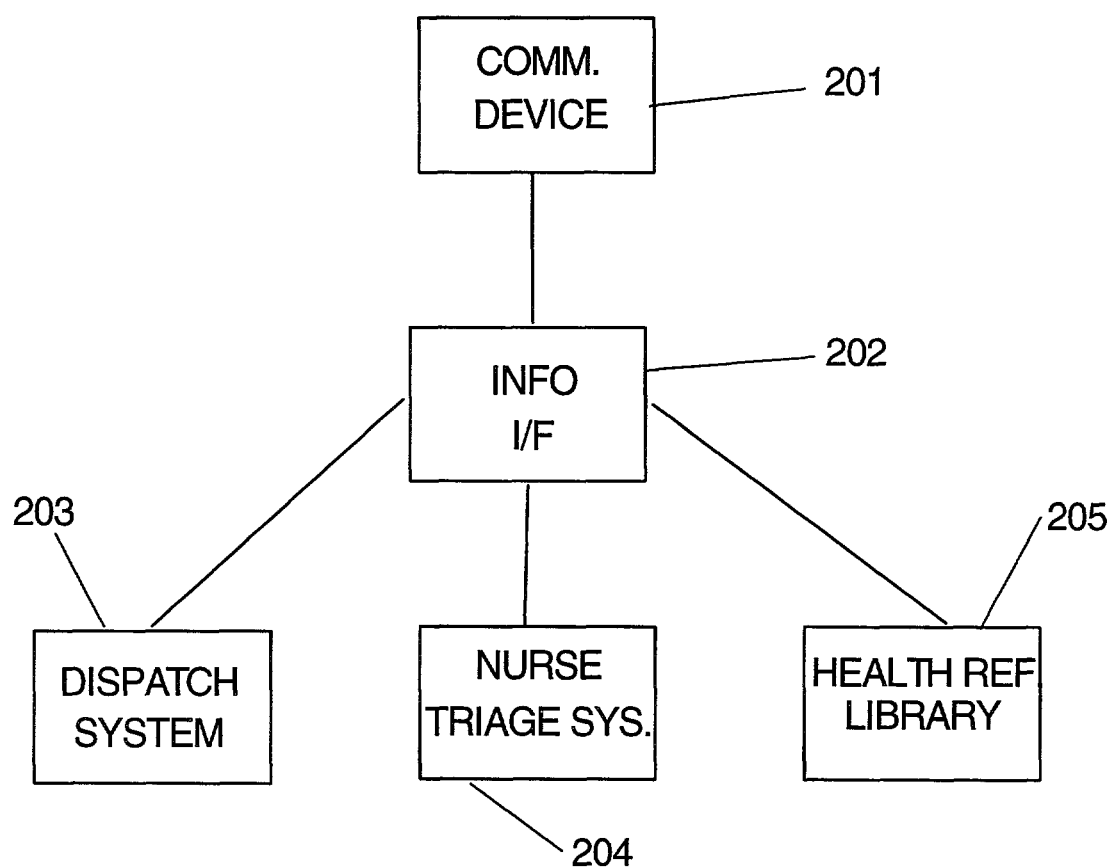
FIG. 2 is a top-level functional block diagram showing the major sections of this invention.

FIG. 2 shows a top-level functional block diagram showing the major sections of this invention. A communication device 201 is provided for receiving calls and for providing medical information to a caller. The present communication device 201 is a telephone, preferably having the capability for caller identification and recording when desired. The information interface 202 provides a clinical link between the emergency medical dispatch system 203, the nurse triage system 204 and the health reference library 205 and includes databases for the storage of patent, incident, medical and protocol information. The emergency medical dispatch system 203 includes protocols or processes for enabling trained call handlers to collect critical information that is used to calculate a criticality determinate value used to determine the appropriate medical response and to provide pre-arrival instructions to callers and dispatched emergency medical personnel. Typically, calls that are non-emergent, are routed to the nurse triage system 204, where queries are made and data is collected using triage processes. For callers who seek health information, the call is routed to the health reference information library 205. It is to be expected that a call may employ some or all of the systems (emergency dispatch system; nurse triage system and the health reference library) and that the call taking process may be routed back and forth between these systems as appropriate to the call. The information interface 202 provides a consistent user interface and a common storage of information so that the routing is transparent to the call taker and so that collected information is available to each system.

The present nurse triage system 204 includes in excess of 180 symptom-specific, gender-specific and age-specific, trinary logic processes that can be used by the call center, typically in non-emergency situations to interpret the symptoms communicated by the callers and to direct these callers to an appropriate level of care or self-management. Each process features a logically structured question sequence that enables the "nurse" to assess the possibility that a serious pathology may underlie the communicated symptoms. Should serious pathology be deemed possible, the process is transferred to the emergency dispatch system 203 along with the information obtained during the call and, sometimes after additional information is collected, the appropriate dispatch code is triggered, based on the calculated determinate criticality value, and the appropriate emergency medical dispatch personnel are dispatched the person requiring medical assistance. The type of dispatch (routine, EMTs, lights and sirens, ambulance, life flight and the like) is determined by the calculated determinate criticality value. Should the call not constitute a medical emergency, the nurse triage system 204 process prompts call center personnel to provide specific interim management instructions, call back instructions and follow-up calls as appropriate. Each nurse triage process of the present nurse triage system 204 consists of an array of flow-control and logic pointers linked to clinical content containing questions and final end point instructions. The questions are dynamically personalized to the caller's demographics in order to foster effective dialogue between the caller and the "nurse" call taker. The various processes of the nurse triage system 204 are preferably IT platform independent, is easily translatable, customizable and up-datable. This flexibility includes the sequence and wording of the questions, the addition or deletion of questions, alterations or additions to caller dispositions, self-care instructions and callback instructions. The processes are further enhanced through linkage to the health reference library 205, as well as including process specific overviews, clinical rationales for each question and references. Since the processes incorporate specifically designed algorithms, the processes provide a reproducible, standardized approach to telephone triage, eliminating unintended variation in questions and call information collection, such as could otherwise occur if a key question were forgotten, or if the caller's underlying illness were not accounted for, or if bias were inadvertently introduced into the call taking process. However, at the same time, the processes permit the appropriate use of discretion by call center "nurses". For example, in the present embodiment of the invention, there is an override "switch" that enables a nurse to select the disposition that he/she feels is the most appropriate. In such cases, the system 204 prompts the nurse to explain why the system's suggested disposition was not invoked, with the answer becoming part of the call record. Nurse call takers also may have the discretionary ability to back-out of questions or even entire processes and to select self-care and callback instructions from a menu.

The present health reference library 205 includes an integrated suite of four HTML based sub-products know as RxView, Clinsights, VxView and HbView. RxView is a medications database that contains comprehensive, user-friendly information about prescription and over-the-counter (OTC) drugs and herbal preparations. For thousands of substances in these three categories, the RxView database includes up-to-date information regarding the following subjects: Proper pronunciation; Use in children; Drug classification; Use in seniors; Indications for use; Use in athletes; Common side effects; How to take the medication; Medications to avoid; Storage instructions; Medications requiring dose change; Special information/cautions; Symptoms of toxicity; generic and other brand names; Use in pregnancy; Name of drug manufacturer; Use while nursing; Special assistance phone lines; Use in infants; Web sites of interest; Use in toddlers. Also, more than 400 herbal preparations are available in the present RxView database, since use of these unregulated compounds is increasing in the general population.

Clinsights is a database that contains user-friendly information regarding several hundred medical conditions, disease states and symptoms, ranging from acne to Zollinger-Ellison syndrome. For each entity in the system, the present Clinsights database includes up-to-date information regarding the following subjects: General overview; Pathophysiology; Incidence and prevalence; Genetic factors; Etiology racial factors; Gender-related factors; Treatments; Age-related factors; Medications; Symptoms; Activity level; Differential diagnosis; Dietary considerations; Risk factors; Symptoms of worsening; Prevention; ICD10-CM code; Expected outcomes; Hotlines and other resources; Complications; References; Laboratory tests; Photographs. In a call center environment, the Clinsights database can be a key reference source for triage nurses. Triage nurses can access the Clinsights database to find answers to the disease-related questions that some callers will have and can use it to improve their understanding of the various symptoms that callers may present during the course of a normal workday.

The VxView database contains pertinent information about all vaccines and immunizations that are in common use at present. These include: Anthraxpertussus; Cholera; Plague; Diphtheria; Pneumococcus; Hemophilus Influenza type B; Poliomyelitis; Hepatitis A; Rabies; Hepatitis B; Rubella; Influenza; Smallpox; Japanese B encephalities; Tetanus; Toxoid; Lyme disease; Tuberculosis; Measles; Typhoid fever; Meningococcus varicella; Mumps; Yellow fever. For each vaccine or immunization, the present VxView database provides current information about the following subjects: Vaccine type; Drug interactions; Immune response; Contraindications; Preparations; Use in pregnancy; Indications; Use while nursing; Side effects; Use in infants; Side effects by preparation; Use in children and teens; Legal issues; References; Schedules. The present VxView contains information that many practitioners do not typically have at their fingertips, since they tend to focus on differential diagnosis and acute care rather than prevention.

The four sub-products contained in the health reference library 205 are housed in a single platform, meaning that call center nurses can operate in an integrated clinical environment from which they can respond to the myriad of non-emergency concerns posed by callers. For example, they can handle drug-related questions and disease-related questions during the same call without having to access text sources or non-integrated databases. This capability results in reduced call time and increased caller satisfaction.

In the present embodiment, all of the medical information contained in the health reference library 205 can be customized. This enables medical leaders from a particular health system to assure that the information contained in the library 205 is what they wish it to be. Information contained within each of the library's 205 four sub-products is parsed into small sections, and each section is accessible using a simple point-and-click approach.

The emergency medical dispatch system 203 of this invention provides a set of symptom-specific procedures to determine the health status of a person who has called an emergency access telephone number. Specific information is collected from the caller. From this specific information, a determinate value of the criticality of the call is calculated. Based on this determinate value, an appropriate level of response is recommended, both in terms of the type of response and the speed with which the response is made. Typical responses may include: call-back later, make an appointment to see a doctor, drive to the nearest hospital, routine dispatch of emergency medical personnel, dispatch urgent emergency medical personnel, dispatch an ambulance, and dispatch a life flight. This present non-linear response methodology of the dispatch system 203 establishes local response assignments to match each MPDS code (disposition) in terms of advanced life support (ALS)/basic life support (BLS) capability, hot/cold response (lights and siren) and multiple or single unit dispatch. The categories of response of the present embodiment include: Delta (ALS Hot), Charlie (ALS Cold), Bravo (BLS Hot), Alpha (BLS Cold) and Omega, in which the call is routed to the nurse triage system 204. Local medical control is used to establish the actual response configurations, regardless of these generic tiers. Further considerations are made and input as to the length of response time and local emergency medical care facility locations. Since the protocols/process of the dispatch system 203 include recommendations and pre-arrival instructions that involve potentially life and death situations, the present dispatch system 203 has been subjected to rigorous medical review. This dispatch system 203 enables the call taker to rapidly and safely navigate through the emergency medical dispatch system protocols, by use of a computer expert system, whereby the key questions and answers are pre-determined in logic to offer an appropriate response determinate. This present dispatch system 203 also is designed to encourage compliance to protocol and to thereby reduce the amount of time spend review cases for compliance. The present dispatch system 203 includes a built-in reporting capability, which facilitates assessments of the performance of call taker staff as well as the entire emergency dispatch center. Such assessments typically include compliance with protocol, call processing time (EMD sections), and peer comparisons. The present embodiment of the dispatch system 203 also has an export data facility that facilitates the importation of data into other database structures in order to augment other statistical data gathered by other dispatch center tools. The dispatch system 203 can also be used to determine the incident code, thereby enabling each dispatch center to tailor the response to meet local medical control parameters and equipment availability.

Figure 3:
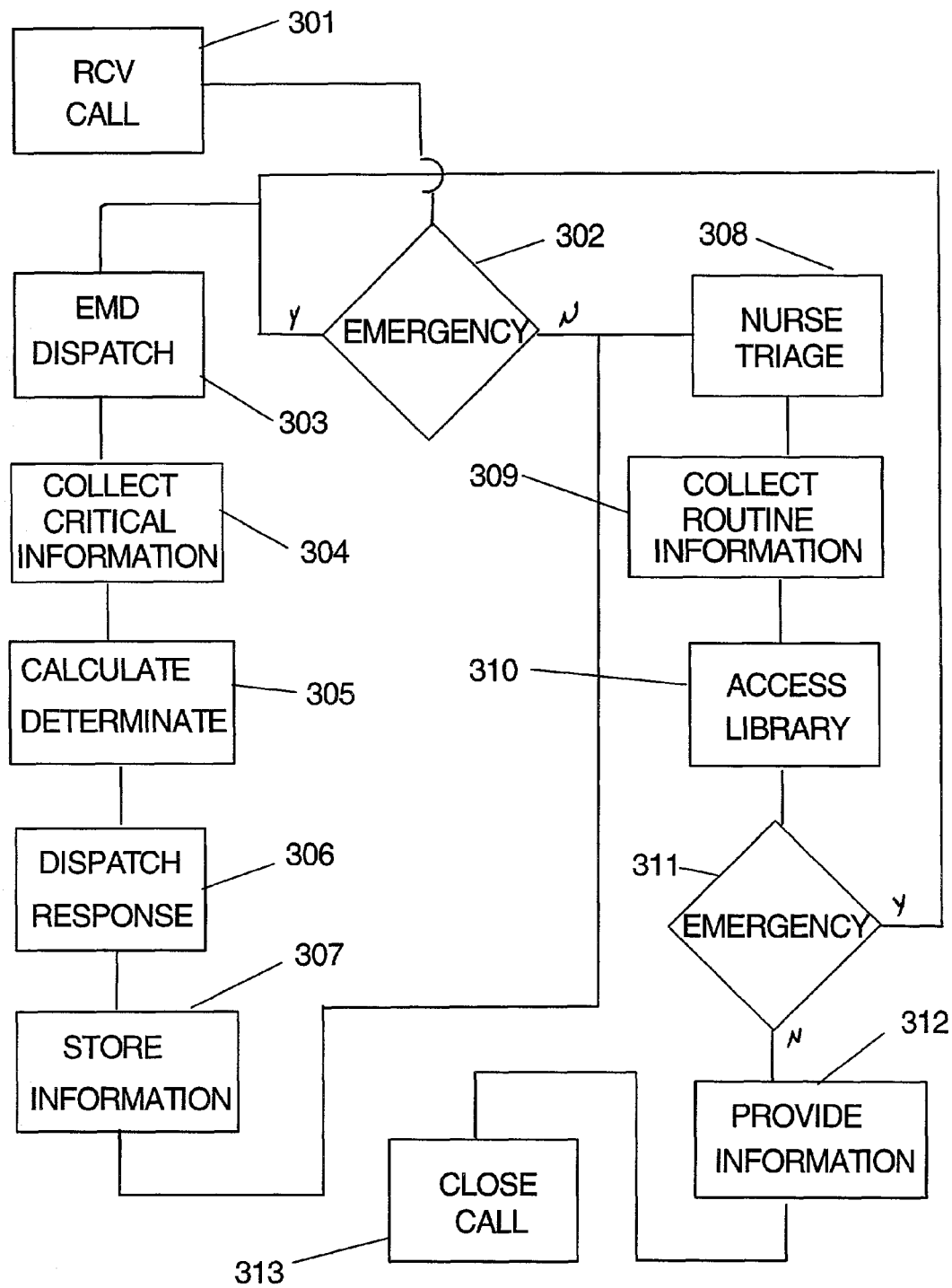
FIG. 3 is a detailed flow chart of the present process steps of this invention.

FIG. 3 shows a detailed flow chart of the present process steps of this invention. The process of this invention provides an interface 202 with an automated integration of an emergency medical dispatch system 203 with a nurse triage system 204 and a health reference library 205, that enables call takers to collect not only health specific information, but also demographic and insurance information about the person needing medical assistance and to provide information to the caller. Initially a call is received 301. A test 302 is made to determine if the call is clearly an emergency. If it is an emergency call then the emergency dispatch system 203 is initiated 303. Generally, the call is transferred to an EMD-capable operator via a message-waiting queue. Times for entry and retrieval from the queue are stored in the call report database. Typically, although not exclusively, the calls are handled by the EMD-capable operator in a first in, first out method. The call taker is prompted to ask and enter specific critical information 304. Using the entered specific critical information the criticality determinate is calculated 305. Depending on the calculated criticality determinate value, an appropriate response is dispatched 306. The collected information is stored 307 and, if appropriate, the process transfers to the initialization 308 of the nurse triage system 204. In the non-emergency cases, the process initiates 308 the nurse triage system 204 wherein typically a nurse call taker is prompted to acquire 309 routine information, including, but not necessarily limited to, demographic and insurance related information. The collection of information 309 includes accessing the appropriate process of the nurse triage system 204, through which health, symptom, malady and/or injury information is collected. The nurse triage system 204 is capable of searching for subscribers, based on subscriber names, dependant name, telephone number, subscriber ID, birth date, address. The default language of the caller along with other subscriber information can be acquired. Interfaces are provided to access 310 the health reference library 205 and other such external data resources as postal databases and out-of-hours answering services. These external data resources may be accessed via electronic protocols, such as TCP/IP and Internet engines, as well as CAD systems, e-mail and faxing services. CTI and ANI/ALI software engines are also used to manage call queuing where appropriate. In the present invention, intranet interface software is used to manage XML content of the dispatch system 203 and the nurse triage system 204. Throughout the nurse triage system 204 tests 311 are made as appropriate to determine if the call is actually an emergency call, in which case the process is routed to the EMD dispatch 303, if the call did not originate with the dispatch system 203. Information is also stored 307 for use by either and both processes 203, 204 of the invention. The present embodiment of the invention is configurable to accept either emergency-only ("first generation" ambulance dispatch) or non-emergency only ("first generation" nurse triage) calls, or to accept both types of calls (Integrated Access Management (IAM)). In this IAM process, call processing begins when the call taker has received a call 301 and selects a "new call" task. This opens a new record in the call database. Each field entry made in the software of the process is data and time stamped along with the recording the call taker identification. The call taker then begins call processing by asking if the call is an emergency 302. Information is typically provided to the caller 312 to assist the caller with the health condition of interest. Once the call process has been completed, there is a brief "post-incident" data collection process, in which the original intention, actual disposition, notes, nurse log/acceptance and record of the caller-call taker is stored to disk with runtime archiving and report generation. This process is considered closing the call 313.

We claim:

1. A computer system for integrating an emergency medical dispatch system and a nurse triage system, comprising:
an emergency medical dispatch system (EMDS) configured to receive health information collected by an EMDS operator and originating from an individual responding to one or more questions asked by the EMDS operator, the questions provided to the EMDS operator by the EMDS computer according to a pre-scripted protocol; and
a nurse triage system (NTS) configured to receive health information collected by an NTS operator and originating from an individual responding to one or more questions asked by the NTS operator, the NTS comprising a test to determine if the received health information reflects an emergency situation; and
an information interface system in communication with the EMDS and the NTS, wherein if the test of the NTS determines the received health information reflects an emergency situation said information interface system provides an automated interface between the EMDS and the NTS by automatically routing the health information received by the NTS to the EMDS to enable use of the health information by the EMDS and eliminate redundant collection of the received health information.

2. A computer system for integrating an emergency medical dispatch system and a nurse triage system, as recited in claim 1, wherein the health information is collected via a call and wherein a call transfer also occurs from the NTS operator to the EMDS operator with the automatic routing of the health information.

3. A computer system for integrating an emergency medical dispatch system and nurse triage system, as recited in claim 1, wherein the EMDS further comprises:
(1) one or more symptom specific protocols; and
(2) a criticality determinate value, wherein the criticality determinate value is used to dispatch an appropriate emergency medical response.

4. A computer system for integrating an emergency medical dispatch system and a nurse triage system, as recited in claim 1, wherein said NTS further comprises:
one or more logic processes;
a set of questions from said one or more logic processes; and
information for providing to a caller based on said set of responses to said set of questions.

5. A computer system for integrating an emergency medical dispatch system and a nurse triage system, as recited in claim 1, wherein said information interface system further comprises:
a route of information from said NTS to said EMDS if it is determined that a call constitutes an emergency call; and
a route of information from said EMDS to said NTS, if additional information after the dispatch of an emergency medical response is available.

6. The computer system of claim 1, wherein said NTS performs a search to locate a subscriber to said system and to acquire subscriber information.

7. The computer system of claim 1, wherein the NTS operator is a trained medical professional.

8. The computer system of claim 1, wherein the NTS operator is also the EMDS operator.

9. The computer system of claim 1, wherein the NTS operator is located at a first call center and the EMDS operator is located at a second call center.

10. The computer system of claim 1, wherein the system further comprises a communication device, and wherein the computer system performs an initial test to make a preliminary determination whether a communication via the communication device pertains to an emergency situation, and if the initial test determines the communication pertains to an emergency situation the EMDS is initiated, and if the initial test determines the communication does not pertain to an emergency situation the NTS is initiated.

11. The computer system of claim 1, wherein the EMDS comprises a test to determine if received health information reflects a non-emergency situation, and wherein if the test of the emergency medical dispatch process determines that the received health information reflects a non-emergency situation, the information interface system automatically routes the health information received by the EMDS to the NTS to enable use of the received health information by the nurse triage process and eliminate redundant collection of the received health information.

12. A computer-implemented method for integrating an emergency medical dispatch system and a nurse triage system, comprising:
    receiving health information on a nurse triage system (NTS) computer, the health information collected by an NTS operator during a health related call from a caller, wherein the caller provides the health information by responding to one or more questions asked by the NTS operator, wherein said NTS comprises a test to determine if the health related call is an emergency call;
    if the health related call is an emergency call, initiating an emergency medical dispatch system (EMDS) on a computer and entering an emergency medical dispatch process, wherein the EMDS is configured to receive health information collected by an EMDS operator from the caller, wherein the health information is provided by the caller responding to one or more questions asked by the EMDS operator, the questions provided to the EMDS operator by the computer of the EMDS according to a pre-scripted protocol; and
    if the health related call is an emergency call, an information interface system computer also automatically routing to the EMDS, from the NTS, the health information received by the NTS prior to determining that the call is an emergency call, whereby the received health information can be used by the EMDS to eliminate redundant collection of the received health information.

13. The computer-implemented method of claim 12, wherein a health related call takes place over a communication device.

14. The computer-implemented method of claim 13, wherein the communication device is a telephone.

15. The computer-implemented method of claim 13, wherein the communication device is a two-way radio.

16. The computer-implemented method of claim 12, wherein the test to determine if a health related call is an emergency call compares received health related information to pre-defined norms.

17. The computer-implemented method of claim 12, further comprising:
    performing a search to locate a subscriber to said system and acquiring subscriber information.

18. The computer-implemented method of claim 12, wherein a health related call involves a live NTS operator talking with a live caller over the telephone.

19. The computer-implemented method of claim 12, wherein the NTS operator is a trained medical professional.

20. The computer-implemented method system of claim 12, wherein the NTS operator is also the EMDS operator.

21. The computer-implemented method of claim 12, wherein the NTS operator and the NTS are located at a first call center and the EMDS operator and EMDS are located at a second call center.

22. The computer-implemented method of claim 12, further comprising:
    receiving a health related call on a communication device coupled to a computer system;
    the computer system performing an initial test to make a preliminary determination whether the health related call is an emergency;
    if the initial test determines the communication pertains to an emergency, the computer system initiating the EMDS and routing the health related call to the EMDS operator; and
    if the initial test determines the health related call is not an emergency the computer system initiating the NTS and routing the call to the NTS operator.

23. The computer-implemented method of claim 12, further comprising
    receiving health information on the EMDS, the health information collected through the EMDS operator during a call from a caller, wherein the caller provides the health information by responding to-one or more questions asked by the EMDS operator, the questions provided to the EMDS operator by the EMDS according to a pre-scripted protocol, wherein said EMDS comprises a test to determine if the health related call is a non-emergency call;
    if the health related call is a non-emergency call, initiating the NTS; and
    if the health related call is a non-emergency call, an information interface system automatically routing to the NTS, from the EMDS, the health information received by the EMDS prior to determining that the call is a non-emergency call, whereby the received health information can be used by the nurse triage process to eliminate redundant collection of the received health information.

24. A method for interfacing an emergency medical dispatch system and a nurse triage system, comprising:
    receiving a medical call;
    determining whether the received medical call is an emergency call;
    entering an emergency dispatch system if the received medical call is an emergency;
    collecting critical health related information;
    calculating a criticality determinate value based on the collected critical health related information;
    dispatching an emergency medical response based on the calculated criticality determinate value;
    storing said collected information and wherein said stored information is stored in a manner that it can be used directly by both the emergency medical dispatch process and a nurse triage system;

entering the nurse triage system, using said collected critical health information, wherein the nurse triage system further comprises testing to determine if a call is an emergency call and rerouting the call to the emergency medical dispatch system from the nurse triage system if the call is determined to be an emergency call; and automatically routing collected medical related information to the emergency medical dispatch system from the nurse triage system if the call is determined to be an emergency call.

25. The method of claim 24, wherein a health related call takes place over a communication device.

26. The method of claim 25, wherein the communication device is a telephone.

27. The method of claim 25, wherein the communication device is a two-way radio.

28. The method of claim 24, further comprising:
performing a search to locate a subscriber to said system and acquiring subscriber information.

29. The method of claim 24, wherein a health related call takes place live in person.

* * * * *